(12) United States Patent
Dolente et al.

(10) Patent No.: US 8,828,989 B2
(45) Date of Patent: Sep. 9, 2014

(54) OXY-CYCLOHEXYL-4H,6H-5-OXA-2,3,10B-TRIAZA-BENZO[E]AZULENES AS V1A ANTAGONISTS

(75) Inventors: Cosimo Dolente, Allschwil (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 189 days.

(21) Appl. No.: 13/592,493

(22) Filed: Aug. 23, 2012

(65) Prior Publication Data

US 2013/0079333 A1 Mar. 28, 2013

(30) Foreign Application Priority Data

Sep. 26, 2011 (EP) .................................. 11182796

(51) Int. Cl.
*A61K 31/553* (2006.01)
*C07D 498/04* (2006.01)

(52) U.S. Cl.
CPC ............ *C07D 498/04* (2013.01); *A61K 31/553* (2013.01)
USPC ........................................ 514/211.1; 540/548

(58) Field of Classification Search
CPC .............................. A61K 31/553; C70D 498/04
USPC ........................................ 514/211.1; 540/548
See application file for complete search history.

(56) References Cited

U.S. PATENT DOCUMENTS

| | | |
|---|---|---|
| 2004/0186091 A1 | 9/2004 | Bryans et al. |
| 2007/0167430 A1 | 7/2007 | Ryckmans |
| 2010/0125066 A1 | 5/2010 | Schnider |
| 2010/0137286 A1 | 6/2010 | Schnider |

FOREIGN PATENT DOCUMENTS

| | | |
|---|---|---|
| WO | 0043398 | 7/2000 |
| WO | 00/78762 A1 | 12/2000 |
| WO | 2005/068466 | 7/2005 |
| WO | 2010/057795 | 5/2010 |
| WO | 2010/060836 | 6/2010 |

OTHER PUBLICATIONS

The English translation of the Taiwanese Office Action, issued on Nov. 25, 2013, in the corresponding Taiwanese application No. 101135168.
Michelini et al., Ann NY Acad Sci 897:198-211 ( 1999).
(International Search Report for PCT/EP2012/068721 Nov. 2, 2012).
Kendler et al., Arch Gen Psychiatry 60:789-796 (Aug. 2003).
Thompson et al., Psychoneuroendocrinology 29:35-48 (2004).
Reiger et al., Brit J of Psychiatry 173(34):24-28 ( 1998).
Robben et al., Am J Physiol Renal Physiol 291:257-270 ( 2006).
Yirmiya et al., Molecular Psychiatry 11:488-494 ( 2006).
Altemus et al., Arch Gen Psychiatry 49:9-20 (Jan. 1992).
Vankerckhoven et al., European Journal of Pharmacology 449:135-141 ( 2002).
Ebner et al., Eur. J. Neuroscience 15:384-388 ( 2002).
Landgraf et al., Reg Peptides 59:229-239 ( 1995).
Raskind et al., Biol. Psychiatry 22:453-462 ( 1987).
Bielsky et al., Neuropsychopharmacology 29:483-493 ( 2004).
The letter of opposition in the corresponding Costa Rican Application No. 2014-0092, which was notified by the Costa Rican Patent Office on Jul. 4, 2014.

*Primary Examiner* — Brenda Coleman

(57) ABSTRACT

The present invention provides 4H,6H-5-oxa-2,3,10b-triaza-benzo[e]azulenes of the formula

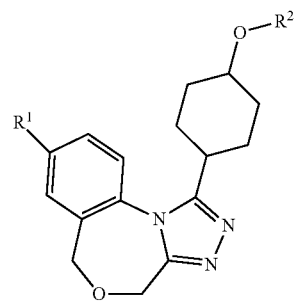

I wherein $R^1$ and $R^2$ are as defined herein and
which act as V1a receptor modulators, and in particular as V1a receptor antagonists, their manufacture, pharmaceutical compositions containing them and their use as medicaments.

6 Claims, No Drawings

OXY-CYCLOHEXYL-4H,6H-5-OXA-2,3,10B-TRIAZA-BENZO[E]AZULENES AS V1A ANTAGONISTS

PRIORITY TO RELATED APPLICATION(S)

This application claims the benefit of European Patent Application No. 11182796.0, filed Sep. 26, 2011, which is hereby incorporated by reference in its entirety.

FIELD OF THE INVENTION

The present invention provides 4H,6H-5-oxa-2,3,10b-triaza-benzo[e]azulenes, which act as V1a receptor modulators, and in particular as V1a receptor antagonists, their manufacture, pharmaceutical compositions containing them and their use as medicaments. The present compounds are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

SUMMARY OF THE INVENTION

The present invention provides a compound of formula I

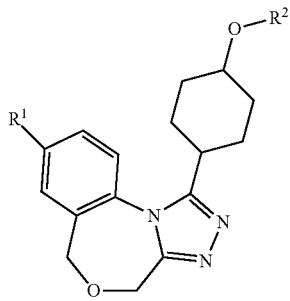

wherein the substituents and variables are as described below and in the claims, or a pharmaceutically acceptable salt thereof.

The present compounds are V1a receptor antagonists, useful for the treatment of depression.

BACKGROUND OF THE INVENTION

Vasopressin is a 9 amino acid peptide mainly produced by the paraventricular nucleus of the hypothalamus. In the periphery vasopressin acts as a neurohormone and stimulates vasoconstriction, glycogenolysis and antidiuresis.

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al. (2006). Am J Physiol Renal Physiol. 291, F257-70, "Cell biological aspects of the vasopressin type-2 receptor and aquaporin 2 water channel in nephrogenic diabetes insipidus"). Compounds with activity at the V2 receptor may therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann (2008). J Neuroendocrinol. 20, 858-65, "Brain oxytocin: a key regulator of emotional and social behaviours in both females and males"). Central oxytocin receptor antagonism might therefore lead to anxiogenic effects, which are regarded as undesired side-effects In the brain vasopressin acts as a neuromodulator and is elevated in the amygdala during stress (Ebner, et al. (2002). Eur J Neurosci. 15, 384-8., "Forced swimming triggers vasopressin release within the amygdala to modulate stress-coping strategies in rats"). It is known that stressful life events can trigger major depression and anxiety (Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety") and that both have very high comorbidity, with anxiety often preceding major depression (Regier, et al. (1998). Br J Psychiatry Suppl. 24-8, "Prevalence of anxiety disorders and their comorbidity with mood and addictive disorders"). The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al. (2004). Neuropsychopharmacology. 29, 483-93, "Profound impairment in social recognition and reduction in anxiety-like behavior in vasopressin V1a receptor knockout mice"). The downregulation of the V1a receptor using antisense oligonucleotide injection in the septum also causes a reduction in anxious behavior (Landgraf, et al. (1995). Regul Pept. 59, 229-39., "V1 vasopressin receptor antisense oligodeoxynucleotide into septum reduces vasopressin binding, social discrimination abilities, and anxiety-related behavior in rats"). Vasopressin or the V1a receptor are also implicated in other neuropsychological disorders: genetic studies recently linked sequence polymorphism in the promoter of the human V1a receptor to autistic spectrum disorders (Yirmiya, et al. (2006). 11, 488-94, "Association between the arginine vasopressin 1a receptor (AVPR1a) gene and autism in a family-based study: mediation by socialization skills"), intranasal administration of vasopressin was shown to influence aggression in human males (Thompson, et al. (2004). Psychoneuroendocrinology. 29, 35-48, "The effects of vasopressin on human facial responses related to social communication") and vasopressin levels were found to be elevated in schizophrenic patients (Raskind, et al. (1987). Biol Psychiatry. 22, 453-62, "Antipsychotic drugs and plasma vasopressin in normals and acute schizophrenic patients") and patients with obsessive-compulsive disorder (Altemus, et al. (1992). Arch Gen Psychiatry. 49, 9-20, "Abnormalities in the regulation of vasopressin and corticotropin releasing factor secretion in obsessive-compulsive disorder").

The V1a receptor is also mediating the cardiovascular effects of vasopressin in the brain by centrally regulating blood pressure and heart rate in the solitary tract nucleus (Michelini and Morris (1999). Ann N Y Acad. Sci. 897, 198-211, "Endogenous vasopressin modulates the cardiovascular responses to exercise"). In the periphery it induces the contraction of vascular smooth muscles and chronic inhibition of the V1a receptor improves hemodynamic parameters in myocardial infarcted rats (Van Kerckhoven, et al. (2002). Eur J Pharmacol. 449, 135-41, "Chronic vasopressin V(1A) but not V(2) receptor antagonism prevents heart failure in chronically infarcted rats"). Hence, V1a antagonists with improved penetration through the blood-brain barrier are expected to be of advantage.

A vasopressin V1a receptor antagonist was shown to be effective in reducing dysmenorrhea in the clinic (Brouard, et al. (2000). Bjog. 107, 614-9, "Effect of SR49059, an orally active V1a vasopressin receptor antagonist, in the prevention of dysmenorrhoea"). V1a receptor antagonism has also been implicated in the treatment of female sexual dysfunction (Aughton, et al. (2008). Br J Pharmacol. doi:10.1038/bjp.2008.253, "Pharmacological profiling of neuropeptides on rabbit vaginal wall and vaginal artery smooth muscle in vitro"). In a recent study V1a receptor antagonists were suggested to have a therapeutic role in both erectile dysfunction and premature ejaculation (Gupta, et al. (2008). Br J Pharmacol. 155, 118-26, "Oxytocin-induced contractions within rat and rabbit ejaculatory tissues are mediated by vasopressin V(1A) receptors and not oxytocin receptors").

DETAILED DESCRIPTION OF THE INVENTION

Object of the present invention is a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with modulation of the V1a receptor, and in particular with V1a receptor antagonism. A further object of the invention is to provide selective inhibitors of the V1a receptor, since selectivity for the V1a receptor is expected to afford a low potential to cause unwanted off-target related side effects such as discussed above.

Present compounds are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior. Particular indications with regard to the present invention are the treatment of anxiety, depressive disorders, obsessive compulsive disorder, autistic spectrum disorders, schizophrenia, and aggressive behavior.

DEFINITIONS

The following definitions of the general terms used in the present description apply irrespectively of whether the terms in question appear alone or in combination with other groups.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" groups have 1 to 4 carbon atoms. Specific groups are isopropyl and sec-butyl.

The term "halogen-$C_{1-6}$-alkyl", alone or in combination with other groups, refers to $C_{1-6}$-alkyl as defined herein, which is substituted by one or multiple halogen, in particular 1-5 halogen, more particular 1-3 halogen ("halogen-$C_{1-3}$-alkyl"), specific 1 halogen or 3 halogen. Particular halogen is fluoro. Particular "halogen-$C_{1-6}$-alkyl" is fluoro-$C_{1-6}$-alkyl.

The term "hydroxy-$C_{1-6}$-alkyl", alone or in combination with other groups, refers to $C_{1-6}$-alkyl as defined herein, which is substituted by one or multiple —OH, in particular 1-2 —OH, more particular 1 —OH.

The term "$C_{1-6}$-alkoxy-$C_{1-6}$-alkyl", alone or in combination with other groups, refers to $C_{1-6}$-alkyl as defined herein, which is substituted by one or multiple $C_{1-6}$-alkoxy group as defined herein, in particular 1-2 $C_{1-6}$-alkoxy groups, more particular 1 $C_{1-6}$-alkoxy group.

The term "cyano", alone or in combination with other groups, refers to N≡C—(NC—).

The term "hydroxy", alone or in combination with other groups, refers to —OH.

The term "halogen", alone or in combination with other groups, denotes chloro (Cl), iodo (I), fluoro (F) and bromo (Br). Particular "halogen" is Cl and F. Specific is Cl.

The term "aryl", alone or in combination with other groups, refers to an aromatic carbocyclic group containing 6 to 14, in particular 6 to 10, carbon atoms and having at least one aromatic ring or multiple condensed rings in which at least one ring is aromatic. Examples of "aryl" groups include benzyl, biphenyl, indanyl, naphthyl, phenyl (Ph) and the like. A particular "aryl" group is phenyl.

The term "heteroaryl", alone or in combination with other groups, refers to an aromatic carbocyclic group of having a single 4 to 8 membered ring or multiple condensed rings containing 6 to 14, in particular 6 to 10 ring atoms and containing 1, 2 or 3 heteroatoms individually selected from N, O and S, in particular N and O, in which group at least one heterocyclic ring is aromatic. Examples of "heteroaryl" groups include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" groups are pyridinyl and pyrazinyl, specific are pyridine-2-yl and pyrazin-2-yl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (isobutoxy), 2-butoxy (sec-butoxy), t-butoxy (tert-butoxy), isopentyloxy (i-pentyloxy) and the like. Particular "$C_{1-6}$-alkoxy" groups have 1 to 4 carbon atoms ("$C_{1-4}$-alkoxy").

The term "halogen-$C_{1-6}$-alkoxy", alone or in combination with other groups, refers to $C_{1-6}$-alkoxy as defined herein, which is substituted by one or multiple halogens, in particular fluoro. A particular "halogen-$C_{1-6}$-alkoxy" group is fluoro-$C_{1-6}$-alkoxy.

The term "$C_{3-7}$-cycloalkyl" denotes a monovalent saturated monocyclic or bicyclic hydrocarbon group of 3 to 6 ring carbon atoms. Bicyclic means consisting of two saturated carbocycles having one or more carbon atoms in common. Particular $C_{3-6}$-cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl groups are bicyclo[2.2.1]heptanyl, or bicyclo[2.2.2]octanyl. A specific example of a "$C_{3-7}$-cycloalkyl" group is cyclopropyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular acids are formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. In particular it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

The term "antagonist" denotes a compound that diminishes or prevents the action of another compound as defined e.g. in Goodman and Gilman's "The Pharmacological Basis of Therapeutics, 7th ed." in page 35, Macmillan Publ. Company, Canada, 1985. In particular, antagonists refers to a compound that attenuates the effect of an agonist. A "competitive antagonist" binds to the same site of a receptor as the agonist but does not activate the receptor, thus blocks the agonist's action. A "non-competitive antagonist" binds to an allosteric (non-agonist) site on the receptor to prevent activation of the receptor. A "reversible antagonist" binds non-covalently to the receptor, therefore can be "washed out". An "irreversible antagonist" binds covalently to the receptor and cannot be displaced by either competing ligands or washing.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

In detail, the present invention provides compounds of the general formula I

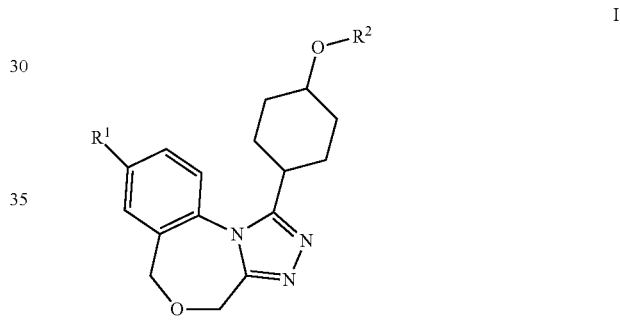

wherein
$R^1$ is halogen, and
$R^2$ is selected from the group consisting of
i) heteroaryl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl;
ii) aryl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl;
iii) $C_{3-7}$-cycloalkyl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl; and
iv) $C_{1-6}$-alkyl, unsubstituted or substituted by 1 to 3 substituents individually selected from the group consisting of OH, halogen, cyano, $C_{1-6}$-alkoxy and halogen-$C_{1-6}$-alkoxy;
or a pharmaceutically acceptable salt thereof.

One embodiment of the invention is a compound of formula I, wherein $R^1$ is chloro.

One embodiment of the invention is a compound of formula I, wherein $R^2$ is selected from the group consisting of unsubstituted heteroaryl, unsubstituted aryl, unsubstituted $C_{3-7}$-cycloalkyl and unsubstituted $C_{1-6}$-alkyl.

One embodiment of the invention is a compound of formula I, wherein $R^2$ is selected from pyridinyl, pyrazinyl, phenyl, cyclopentyl, isopropyl and sec-butyl.

One embodiment of the invention is a compound of formula I, wherein $R^2$ is selected from pyridin-2-yl, pyrazin-2-yl, phenyl, cyclopentyl, isopropyl and sec-butyl.

One embodiment of the invention is a compound of formula I, wherein $R^2$ is heteroaryl.

One embodiment of the invention is a compound of formula I, wherein $R^2$ is pyridinyl.

One embodiment of the invention is a compound of formula I, wherein $R^2$ is pyrazinyl.

One embodiment of the invention is a compound of formula I, wherein $R^2$ is aryl.

One embodiment of the invention is a compound of formula I, wherein $R^2$ is phenyl One embodiment of the invention is a compound of formula I, wherein $R^2$ is $C_{3-7}$-cycloalkyl.

One embodiment of the invention is a compound of formula I, wherein $R^2$ is cyclopentyl.

One embodiment of the invention is a compound of formula I, wherein $R^2$ is $C_{1-6}$-alkyl.

One embodiment of the invention is a compound of formula I, wherein $R^2$ is isopropyl.

One embodiment of the invention is a compound of formula I, wherein $R^2$ is sec-butyl.

One embodiment of the invention is a compound of formula I selected from the group consisting of
8-Chloro-1-(4-isopropoxy-cyclohexyl)-4H,6H-5-oxa-2,3,10b-triaza-benzo[e]azulene,
1-(4-sec-Butoxy-cyclohexyl)-8-chloro-4H,6H-5-oxa-2,3,10b-triaza-benzo[e]azulene,
8-Chloro-1-(4-cyclopentyloxy-cyclohexyl)-4H,6H-5-oxa-2,3,10b-triaza-benzo[e]azulene,
8-Chloro-1-(4-phenoxy-cyclohexyl)-4H,6H-5-oxa-2,3,10b-triaza-benzo[e]azulene,
8-Chloro-1-[4-(pyridin-2-yloxy)-cyclohexyl]-4H,6H-5-oxa-2,3,10b-triaza-benzo[e]azulene, and
8-Chloro-1-[4-(pyrazin-2-yloxy)-cyclohexyl]-4H,6H-5-oxa-2,3,10b-triaza-benzo[e]azulene,
or a pharmaceutically acceptable salt thereof.

One embodiment of the invention is a compound of formula I, which is 8-Chloro-1-(4-isopropoxy-cyclohexyl)-4H,6H-5-oxa-2,3,10b-triaza-benzo[e]azulene.

One embodiment of the invention is a compound of formula I, which is 1-(4-sec-Butoxy-cyclohexyl)-8-chloro-4H,6H-5-oxa-2,3,10b-triaza-benzo[e]azulene.

One embodiment of the invention is a compound of formula I, which is 8-Chloro-1-(4-cyclopentyloxy-cyclohexyl)-4H,6H-5-oxa-2,3,10b-triaza-benzo[e]azulene.

One embodiment of the invention is a compound of formula I, which is 8-Chloro-1-(4-phenoxy-cyclohexyl)-4H,6H-5-oxa-2,3,10b-triaza-benzo[e]azulene One embodiment of the invention is a compound of formula I, which is 8-Chloro-1-[4-(pyridin-2-yloxy)-cyclohexyl]-4H,6H-5-oxa-2,3,10b-triaza-benzo[e]azulene.

One embodiment of the invention is a compound of formula I, which is 8-Chloro-1-[4-(pyrazin-2-yloxy)-cyclohexyl]-4H,6H-5-oxa-2,3,10b-triaza-benzo[e]azulene.

One embodiment of the invention is a process for synthesis a compound of formula I as described herein, which process comprises reacting a compound of formula II with a compound of formula III to a compound of formula I wherein $R^1$ and $R^2$ are as defined herein.

One embodiment of the invention is a compound of formula I, whenever prepared by a process as defined herein.

One embodiment of the invention is a compound of formula I for use as therapeutically active substance.

One embodiment of the invention is a compound of formula I for the use as therapeutically active substance for the therapeutic and/or prophylactic treatment of diseases and disorders which are associated with V1a receptor antagonism.

One embodiment of the invention is a compound of formula I for the use as therapeutically active substance acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

One embodiment of the invention is a pharmaceutical composition comprising a compound of formula I as described herein and a pharmaceutically acceptable carrier and/or a pharmaceutically acceptable auxiliary substance.

One embodiment of the invention provides the use of a compound of formula I as described herein for the manufacture of a medicament for acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

One embodiment of the invention provides to a method for the use of a compound as described herein, which is acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior, which method comprises administering said compound of formula I to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric centre of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

This applies in particular to the alkylcyclohexylether-head group (HG) of the compounds of formula I, namely

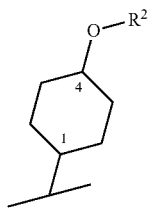

HG wherein at least the carbon atoms 1 and 4 are asymmetric carbon atoms and $R^2$ could further comprise asymmetric carbon atoms. It is to be understood that present invention includes all individual stereoisomers of head groups and mixtures thereof.

Examples of these head groups HG are depicted below, a specific example is HG-4.

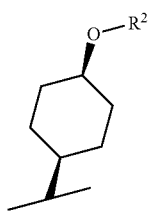

HG-1

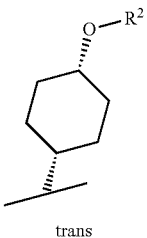

HG-2 trans

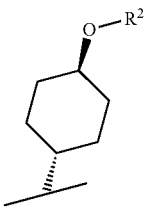

HG-3

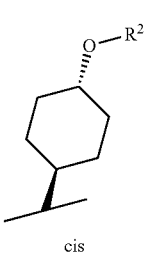

HG-4 cis

It is further understood that all embodiments of the invention as described herein may be combined with each other.

In the embodiments, where optically pure enantiomers are provided, optically pure enantiomer means that the compound contains >90% of the desired isomer by weight, in particular >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I may be prepared in accordance with the following schemes. The starting material is commercially available or may be prepared in accordance with known methods. Any previously defined residues and variables will continue to have the previously defined meaning unless otherwise indicated.

The compounds of formula I can be prepared through a number of synthetic routes for example as illustrated in below schemes. The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

In a certain embodiment, the compounds of formula (I) of the invention can be manufactured according to a process comprising the step of reacting a compound of formula (II)

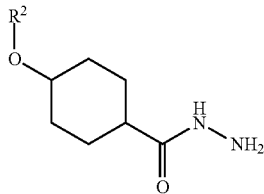

II with a compound of formula (III)

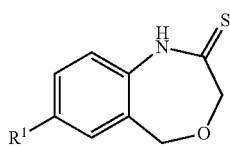

III to obtain a compound of formula (I) wherein $R^1$ and $R^2$ are as defined herein for formula I.

The processes are described in more detail with the following general schemes and procedures A to G.

Scheme 1: General Scheme A

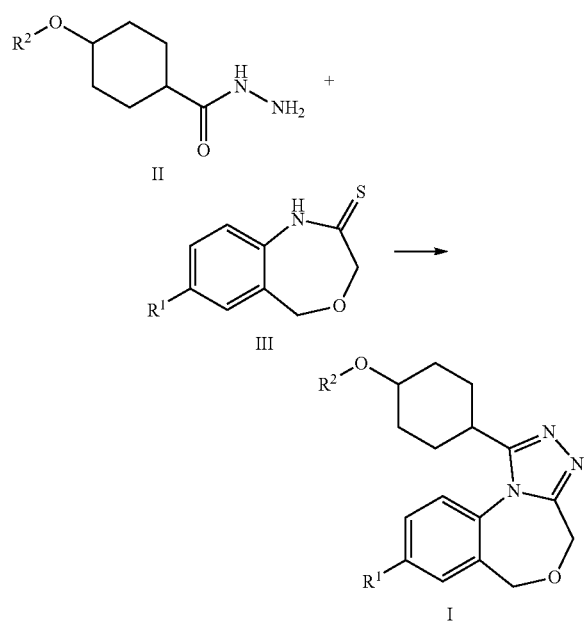

Compounds of formula (I) can be prepared by thermal condensation of a hydrazide derivative of formula (II) and a thiolactam derivative of formula (III). The synthesis of compounds of formula (II) is outlined in general schemes C-G hereinafter. Compounds of formula (III) can be prepared following the general scheme B as described hereinafter. General scheme A is hereinafter further illustrated by general procedure V.

Scheme 2: General Scheme B

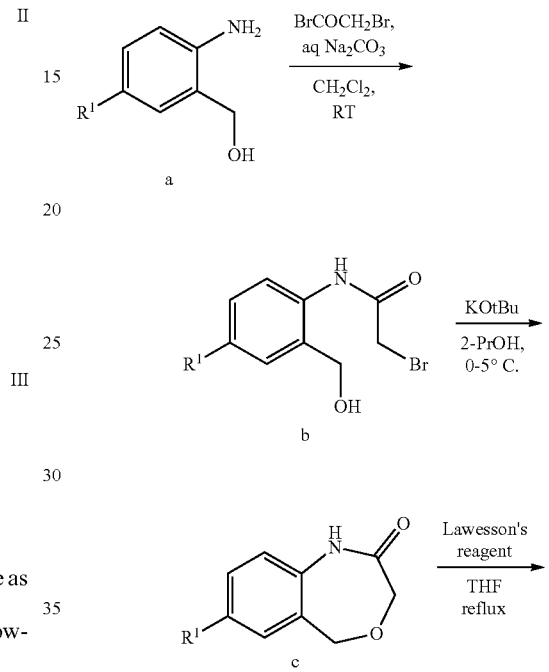

Thiolactam derivatives of formula (III-1) can be obtained as follows: Acylation of a 2-aminobenzyl alcohol of formula (a) to a bromo acetamide ($BrCOCH_2Br$) of formula (b) can be achieved under Schotten-Baumann conditions (biphasic aqueous basic conditions e.g. aqueous sodium carbonate (aq $Na_2CO_3$)) in quantitative yield. Cyclization of a compound of formula (b) with potassium tert-butoxide i(KOtBu) n 2-propanol (2-PrOH) at low temperatures gives compounds of formula (c). A thiolactam derivative of formula (III) is obtained by treatment of a compound of formula (c) with Lawesson's reagent (2,4-bis-(4-methoxyphenyl)-1,3,2,4-dithiadiphosphetane-2,4-disulfide) or phosphorous pentasulfide at elevated temperature in an appropriate solvent (e.g. tetrahydrofurane (THF)).

Scheme 3: General Scheme C

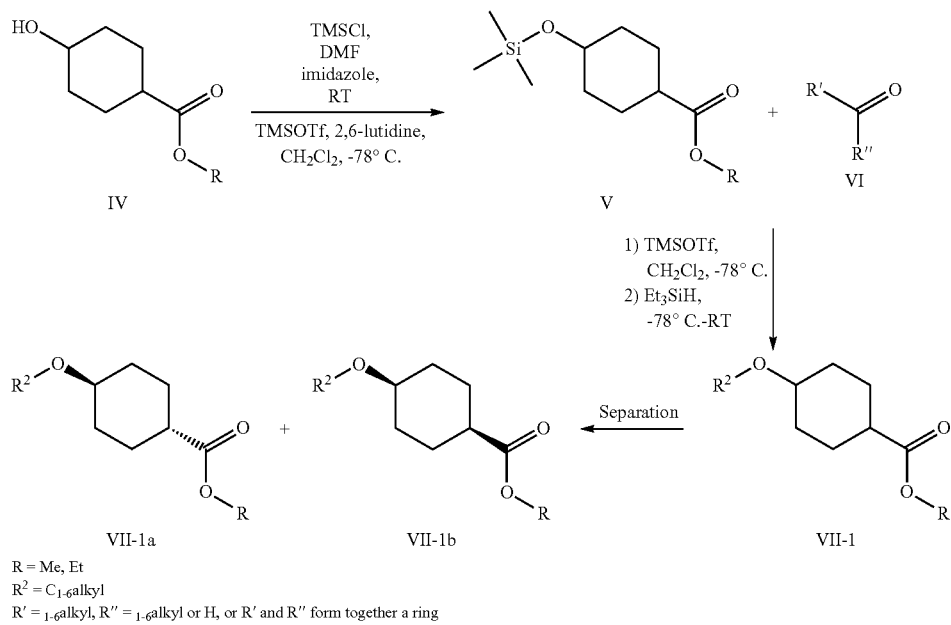

R = Me, Et
R² = C₁₋₆alkyl
R' = ₁₋₆alkyl, R" = ₁₋₆alkyl or H, or R' and R" form together a ring 4-Alkoxy-cyclohexanecarboxylic acid ester derivatives of formula (VII-1) can be obtained by reductive etherification as follows: A 4-hydroxy-cyclohexanecarboxylic acid ester (IV) is converted to a 4-trimethylsilanyloxy-cyclohexanecarboxylic acid ester (V) by O-silylation methods known in the art, e.g. by treatment with a silylating agent such as trimethylsilyl chloride (TMSCl) or trimethylsilyl triflate (TMSOTf) in the presence of a base such as imidazole or 2,6-lutidine in a suitable solvent such as N,N-dimethylformamide (DMF) or dichloromethane (CH$_2$I$_2$). Consecutive treatment of a 4-trimethylsilanyloxy-cyclohexanecarboxylic acid ester (V) and a ketone or aldehyde of formula (VI) with trimethylsilyl triflate in dichloromethane and a reducing agent such as triethylsilane (Et$_3$SiH) leads to 4-alkoxy-cyclohexanecarboxylic acid ester derivatives of formula (VII-1) at room temperature (RT). Compounds of formula (VII-1) are usually obtained as a mixture of cis- and trans-isomers, which can in some cases be separated chromatographically to give the pure trans-4-alkoxy-cyclohexanecarboxylic acid ester of formula (VII-1a) and cis-4-alkoxy-cyclohexanecarboxylic acid ester of formula (VII-1b). General scheme C is hereinafter further illustrated by general procedure I.

Scheme 4: General Scheme D

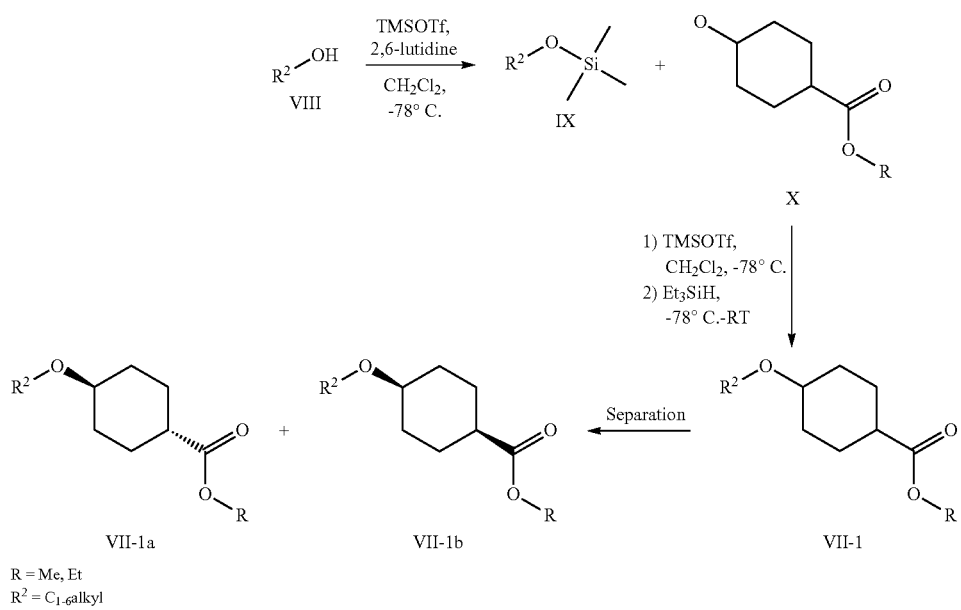

R = Me, Et
R² = C₁₋₆alkyl

Alternatively, 4-alkoxy-cyclohexanecarboxylic acid ester derivatives of formula (VII-1) can be obtained by reductive etherification as follows: Consecutive treatment of an alkoxy-trimethyl-silane of formula (IX) and 4-cyclohexanonecarboxylic acid ethyl ester (X) with trimethylsilyl triflate in dichloromethane and a reducing agent such as triethylsilane gives 4-alkoxy-cyclohexanecarboxylic acid ester derivatives of formula (VII-1). Compounds of formula (VII-1) are usually obtained as a mixture of cis- and trans-isomers, which can in some cases be separated chromatographically to give the pure trans-4-alkoxy-cyclohexanecarboxylic acid ester of formula (VII-1a) and cis-4-alkoxy-cyclohexanecarboxylic acid ester of formula (VII-1b). Alkoxy-trimethyl-silane derivatives of formula (IX) are either commercially available or are prepared using O-silylation methods known in the art, e.g. by treating an alcohol of general formula (VIII) with a silylating agent such as trimethylsilyl chloride or trimethylsilyl triflate in the presence of a base such as imidazole or 2,6-lutidine in a suitable solvent such as N,N-dimethylformamide or dichloromethane. Alternatively, alkoxy-trimethylsilane derivatives of formula (IX) can be prepared in situ without isolation prior to the reductive etherification step with 4-cyclohexanonecarboxylic acid ethyl ester (X) by treating an alcohol of general formula (VIII) with trimethylsilyl triflate and 2,6-lutidine in dichloromethane. General scheme D is hereinafter further illustrated by general procedures IIA and IIB.

Scheme 5: General Scheme E

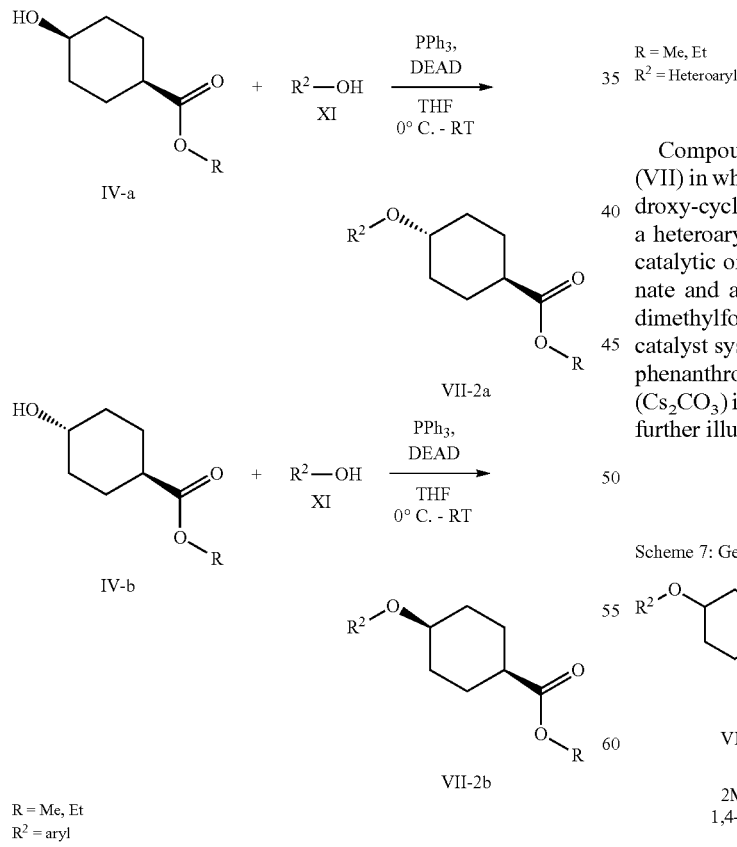

R = Me, Et
R² = aryl

Etherification of a 4-hydroxy-cyclohexanecarboxylic acid ester of formula (IV) with a phenol derivative of formula (XI) under Mitsunobu conditions (diethylazodicarboxylate (DEAD) and triphenylphosphine (PPh₃)) leads to a 4-aryloxy-cyclohexanecarboxylic acid ester of formula (VII-2) under inversion of configuration. Thus trans-4-aryloxy-cyclohexanecarboxylic acid esters of formula (VII-2a) are obtained from a cis-4-hydroxy-cyclohexanecarboxylic acid ester of formula (IV-a), while cis-4-aryloxy-cyclohexanecarboxylic acid esters of formula (VII-2b) are obtained from a trans-4-hydroxy-cyclohexanecarboxylic acid ester of formula (IV-b). General scheme E is hereinafter further illustrated by general procedure IIIA.

Scheme 6: General Scheme F

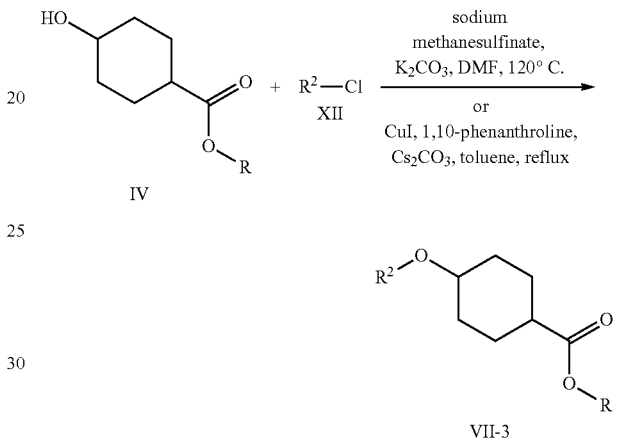

R = Me, Et
R² = Heteroaryl

Compounds of formula (VII-3) (compounds of formula (VII) in which R² is heteroaryl) can be prepared from a 4-hydroxy-cyclohexanecarboxylic acid ester of formula (IV) and a heteroaryl chloride of formula (XII) in the presence of a catalytic or stoichiometric amount of sodium methanesulfinate and a base such as potassium carbonate ($K_2CO_3$) in dimethylformamid (DMF) at 120° C. or in the presence of a catalyst system formed from cuprous iodide (CuI) and 1,10-phenanthroline and a base such as cesium carbonate ($Cs_2CO_3$) in toluene at reflux. General scheme F is hereinafter further illustrated by general procedures IIIB and IIIC.

Scheme 7: General Scheme G

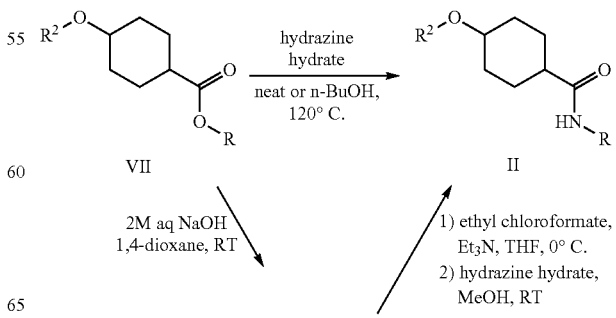

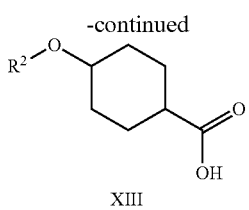

R = Me, Et

A 4-alkoxy- or aryloxycyclohexanecarboxylic acid ester of formula (VII) can be converted to a hydrazide derivative of formula (II) by heating with hydrazine hydrate in an appropriate solvent like n-butanol (n-BuOH). Alternatively, an ester derivative of formula (VII) can be hydrolyzed to a carboxylic acid derivative of formula (XIII) using a biphasic mixture of aqueous sodium or potassium hydroxide solution (NaOH or KOH) and an etheral solvent such as dioxan. A hydrazide derivative of formula (II) can be obtained by activating an acid intermediate of formula (XIII), e.g. with ethyl chloroformate, thionyl chloride, oxalyl chloride or an amide coupling reagent (like triethyl amine ($Et_3N$)), and subsequent coupling with hydrazine. General scheme G is hereinafter further illustrated by general procedure IV.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM $MgCl_2$ adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43,000 g at 4° C. (19,000 rpm). The pellet is resuspended in 12.5 ml Lysis buffer+12.5 ml Sucrose 20% and homogenized using a Polytron for 1-2 min. The protein concentration is determined by the Bradford method and aliquots are stored at −80° C. until use. For binding studies 60 mg Yttrium silicate SPA beads (Amersham) are mixed with an aliquot of membrane in binding buffer (50 mM Tris, 120 mM NaCl, 5 mM KCl, 2 mM $CaCl_2$, 10 mM $MgCl_2$) for 15 minutes with mixing. 50 μl of bead/membrane mixture is then added to each well of a 96 well plate, followed by 50 μl of 4 nM 3H-Vasopressin (American Radiolabeled Chemicals). For total binding measurement 100 μl of binding buffer are added to the respective wells, for non-specific binding 100 μl of 8.4 mM cold vasopressin and for compound testing 100 μl of a serial dilution of each compound in 2% DMSO. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an IC 50 the curve is fitted using a non-linear regression model (XLfit) and the Ki is calculated using the Cheng-Prussoff equation.

The following representative data show the antagonistic activity against human V1a receptor of compounds according to present invention:

TABLE 1 pKi values of selected examples

| Ex. | Structure | pKi hV1a |
|---|---|---|
| 1 | 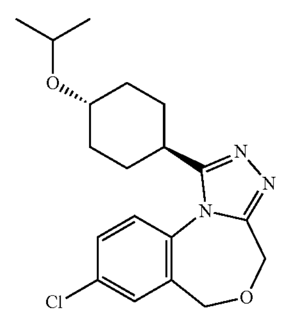 [SMILES: CC(C)O[C@H]1CC[C@H](c2nnc3n2-c2ccc(Cl)cc2COC3)CC1] | 7.72 |
| 2 | 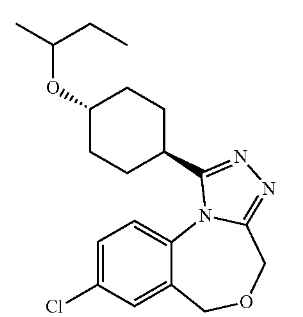 [SMILES: CCC(C)O[C@H]1CC[C@H](c2nnc3n2-c2ccc(Cl)cc2COC3)CC1] | 8.36 |

TABLE 1-continued pKi values of selected examples

| Ex. | Structure | pKi hV1a |
|---|---|---|
| 3 | (cyclopentyloxy-cyclohexyl triazolo-benzoxazepine with Cl) | 9.39 |
| 4 | (phenoxy-cyclohexyl triazolo-benzoxazepine with Cl) | 8.88 |
| 5 | (pyridin-2-yloxy-cyclohexyl triazolo-benzoxazepine with Cl) | 8.63 |
| 6 | (pyrazin-2-yloxy-cyclohexyl triazolo-benzoxazepine with Cl) | 7.57 |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, in particular 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |

TABLE 2-continued possible tablet composition

| ingredient | mg/tablet | | | |
|---|---|---|---|---|
| | 5 | 25 | 100 | 500 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

The following examples are provided for illustration of the invention. They should not be considered as limiting the scope of the invention, but merely as being representative thereof.

Intermediate of Formula (V)

cis/trans-4-Trimethylsilanyloxy-cyclohexanecarboxylic acid ethyl ester (2:1)

To a solution of cis/trans-4-hydroxycyclohexane carboxylic acid ethyl ester (2:1) (5.0 g, 29 mmol) and imidazole (4.4 g, 64 mmol) in N,N-dimethylformamide (90 ml) was added trimethylsilyl chloride (4.0 ml, 32 mmol) at 0-5° C. Stirring for 1 h at room temperature was followed by partitioning between tert-butyl methyl ether (300 ml) and water (150 ml). The layers were separated. The organic layer was washed with two 150-ml portions of water and one 50-ml portion of brine, dried over anhydrous sodium sulfate and concentrated in vacuo to give the title compound (6.7 g, 94%) as colorless oil. MS m/e: 245 ([M+H]$^+$).

4-Alkoxy-cyclohexanecarboxylic acid ester intermediates of formula (VII-1)

Reductive Etherification

General Procedure I

To a solution of cis/trans-4-trimethylsilanyloxy-cyclohexanecarboxylic acid ethyl ester (2:1) in dichloromethane (0.1 M) are added consecutively a ketone or an aldehyde of formula (VI) (0.85 eq) and trimethylsilyl trifluoromethanesulfonate (0.10 eq) at −78° C. The reaction mixture is stirred for 1 h. After addition of triethylsilane (1 eq) the cooling bath is removed and the reaction mixture is allowed to warm to room temperature. Stirring is continued over night. The mixture is quenched with saturated aqueous sodium bicarbonate solution. The layers are separated. The organic layer is dried over anhydrous sodium sulfate and concentrated in vacuo. Purification by flash-chromatography gives a 4-alkoxy-cyclohexanecarboxylic acid ester intermediate of formula (VII-1).

General Procedure IIA

An alkoxy-trimethyl-silane intermediate of formula (IX) is formed in situ by adding trimethylsilyl trifluoromethanesulfonate (1 eq) to a solution of an alcohol derivative of formula (VIII) (1 eq) and 2,6-lutidine (1 eq) in dichloromethane (0.1 M) at −78° C. After 1 h a 4-cyclohexanonecarboxylic acid ester of formula (X) (0.85 eq) and trimethylsilyl trifluoromethanesulfonate (0.1 eq) are added consecutively. The reaction mixture is stirred for 1 h. After addition of triethylsilane (2 eq) the cooling bath is removed and the reaction mixture is allowed to warm to room temperature. Stirring is continued over night. The mixture is quenched with saturated aqueous sodium bicarbonate solution. The layers are separated. The organic layer is dried over anhydrous sodium sulfate and concentrated in vacuo. Purification by flash-chromatography gives a 4-alkoxy-cyclohexanecarboxylic acid ester intermediate of formula (VII-1).

General Procedure IIB

A trimethylsilyloxy intermediate of formula (IX), which is commercially available or which can be prepared according to methods known in the art, is dissolved in dichloromethane (0.1 M). A 4-cyclohexanonecarboxylic acid ester of formula (X) (0.85 eq) and trimethylsilyl trifluoromethanesulfonate (0.1 eq) are added consecutively at −78° C. The reaction mixture is stirred for 1 h. After addition of triethylsilane (2 eq) the cooling bath is removed and the reaction mixture is allowed to warm to room temperature. Stirring is continued over night. The mixture is quenched with saturated aqueous sodium bicarbonate solution. The layers are separated. The organic layer is dried over anhydrous sodium sulfate and concentrated in vacuo. Purification by flash-chromatography gives a 4-alkoxy-cyclohexanecarboxylic acid ester intermediate of formula (VII-1).

4-Alkoxy-cyclohexanecarboxylic acid ester 1 trans-4-Isopropoxy-cyclohexanecarboxylic acid ethyl ester trans-4-Isopropoxy-cyclohexanecarboxylic acid ethyl ester was obtained as colorless oil in 23% yield from acetone according to general procedure I after purification by flash-column chromatography. MS m/e: 214 (M$^+$)

4-Alkoxy-cyclohexanecarboxylic acid ester 2

(RS)-trans-4-sec-Butoxy-cyclohexanecarboxylic acid ethyl ester (RS)-trans-4-sec-Butoxy-cyclohexanecarboxylic acid ethyl ester was obtained as colorless oil in 22% yield from 2-butanone according to general procedure I after purification by flash-column chromatography. MS (EI) m/e: 228 (M$^+$, 1%), 199 ([M-C$_2$H$_5$]$^+$, 6%), 155 ([M-C$_4$H$_9$O]$^+$, 100%)

4-Alkoxy-cyclohexanecarboxylic acid ester 3 trans-4-Cyclopentyloxy-cyclohexanecarboxylic acid ethyl ester trans-4-Cyclopentoxy-cyclohexanecarboxylic acid ethyl ester was obtained as colorless oil in 22% yield from cyclopentanone according to general procedure I after purification by flash-column chromatography. MS (EI) m/e: 240 (M$^+$, 1%), 155 [M-C$_5$H$_9$O]$^+$, 30%)

4-Aryloxy-cyclohexanecarboxylic acid ester intermediates of formula (VII-2) and (VII-3)

General Procedure IIIA: Etherification Under Mitsunobu Conditions

To a solution of triphenylphosphine (1.2 eq) in dry tetrahydrofuran (0.1 M) is added diethyl azodicarboxylate (1.2 eq) at 0° C. After 20 min a phenol derivative of formula (XI) (1.2 eq) and a solution of a 4-hydroxy-cyclohexanecarboxylic acid ester of formula (IV) in tetrahydrofuran (1-3 M) are added consecutively at 5° C. After completed addition the cooling bath is removed and the reaction mixture is allowed to warm to room temperature and stirred for 3-18 h. The solvent is evaporated and the residue is dissolved in ethyl acetate. The ethyl acetate solution is washed with one to two portions of 1 M aqueous sodium hydroxide solution. The aqueous layer is extracted with one to two portions of ethyl acetate. The combined organic layers are dried over anhydrous sodium sulfate and concentrated in vacuo. Purification by flash-chromatography gives a 4-aryloxy-cyclohexanecarboxylic acid ester of formula (VII-2).

General Procedure IIIB: Sodium Methanesulfinate Mediated Arylation

To a solution of a 4-hydroxy-cyclohexanecarboxylic acid ester of formula (IV) (1 eq) and a heteroaryl chloride derivative of formula (XII) (1 eq) in dry N,N-dimethylformamide (1 M) are added consecutively sodium methanesulfinate (85%, 0.25-1 eq) and potassium carbonate (1.5 eq). After completed addition the reaction mixture is stirred at 120° C. for 3-18 h. After cooling to room temperature the reaction mixture is partitioned between tert-butyl methyl ether and water. The layers are separated and the aqueous layer is extracted with one to two portions of tert-butyl methyl ether. The combined organic layers are washed with one to two portions of water, dried over anhydrous sodium sulfate and concentrated in vacuo. Purification by flash-chromatography gives a 4-heteroaryloxy-cyclohexanecarboxylic acid ester of formula (VII-3).

General Procedure IIIC: Copper Catalyzed Arylation

To a mixture of cuprous iodide (0.1 eq), 1,10-phenanthroline (0.2 eq) and a heteroaryl chloride derivative of formula (XII) (1 eq) in toluene (2 M) are added a 4-hydroxy-cyclohexanecarboxylic acid ester of formula (IV) (1 eq) and cesium carbonate (2 eq). The reaction mixture is heated at reflux for 20 h. After cooling to room temperature the reaction mixture is partitioned between ethyl acetate and water. The layers are separated and the aqueous layer is extracted with one to two portions of ethyl acetate. The combined organic layers are washed with one to two portions of 0.5 aqueous hydrogen chloride solution, dried over anhydrous sodium sulfate and concentrated in vacuo. Purification by flash-chromatography gives a 4-heteroaryloxy-cyclohexanecarboxylic acid ester of formula (VII-3).

4-Aryloxy-cyclohexanecarboxylic acid ester 1 trans-4-Phenoxy-cyclohexanecarboxylic acid methyl ester

The title compound was obtained as colorless oil in 23% yield according to general procedure IIIA from phenol and trans-4-hydroxy-cyclohexanecarboxylic acid methyl ester. MS m/e: 234 (M$^+$).

4-Aryloxy-cyclohexanecarboxylic acid ester 2 trans-4-(Pyridin-2-yloxy)-cyclohexanecarboxylic acid methyl ester

The title compound was obtained as light red solid in 36% yield according to general procedure IIIA from 2-hydroxypyridine and trans-4-hydroxy-cyclohexanecarboxylic acid methyl ester. MS m/e: 236 ([M+H]$^+$).

4-Aryloxy-cyclohexanecarboxylic acid ester 3 cis/trans-4-(Pyrazin-2-yloxy)-cyclohexanecarboxylic acid ethyl ester (1:1)

The title compound was obtained as white solid in 15% yield according to general procedure IIIB from 2-chloropyrazine and cis/trans-4-hydroxy-cyclohexanecarboxylic acid ethyl ester ester (2:1). MS m/e: 251 ([M+H]$^+$).

Hydrazide Intermediates of Formula (II)

General Procedure IV: Hydrazide Formation from a 4-alkoxy- or 4-aryloxy-cyclohexanecarboxylic acid ester A mixture of a 4-alkoxy- or 4-aryloxy-cyclohexanecarboxylic acid ester of formula (VII) (1 eq) and hydrazine hydrate (2-6 eq) in n-butanol (0.2-1 M) is heated at reflux for 16-72 h. After cooling to room temperature the reaction mixture is partitioned between an organic solvent such as ethyl acetate or dichloromethane and water. The layers are separated and the aqueous layer is extracted with two portions of organic solvent. The combined organic layers are dried over anhydrous sodium sulfate and concentrated in vacuo to give a crude hydrazide derivate of formula (II), which can usually be used in the next step without further purification.

Hydrazide 1 trans-4-Isopropoxy-cyclohexanecarboxylic acid hydrazide

The title compound was obtained as off-white solid in 70% yield from trans-4-isoproxy-cyclohexanecarboxylic acid ethyl ester according to general procedure IV.
MS m/e: 201 ([M+H]$^+$)

Hydrazide 2

(RS)-trans-4-sec-Butoxy-cyclohexanecarboxylic acid hydrazide

The title compound was obtained as white solid in 93% yield from (RS)-trans-4-sec-butoxy-cyclohexanecarboxylic acid ethyl ester according to general procedure IV.
MS (EI) m/e: 214 (M$^+$)

Hydrazide 3 trans-4-Cyclopentyloxy-cyclohexanecarboxylic acid hydrazide

The title compound was obtained as white solid in 80% yield from trans-4-cyclopentyloxy-cyclohexanecarboxylic acid ethyl ester according to general procedure IV.
MS (EI) m/e: 226 (M$^+$)

Hydrazide 4 trans-4-Phenoxy-cyclohexanecarboxylic acid hydrazide

The title compound was obtained as white solid in quantitative yield from trans-4-phenoxy-cyclohexanecarboxylic acid methyl ester according to general procedure IV.
MS m/e: 235 ([M+H]$^+$)

Hydrazide 5 trans-4-(Pyridin-2-yloxy)-cyclohexanecarboxylic acid hydrazide

The title compound was obtained as white solid in 96% yield from trans-4-(pyridin-2-yloxy)-cyclohexanecarboxylic acid methyl ester according to general procedure IV.
MS m/e: 236 ([M+H]$^+$)

Hydrazide 6 trans-4-(Pyrazin-2-yloxy)-cyclohexanecarboxylic acid hydrazide

A mixture of cis/trans-4-(pyrazin-2-yloxy)-cyclohexanecarboxylic acid ethyl ester (1.11 g, 4.41 mmol) and hydrazine hydrate (0442 g, 8.83 mmol) was heated at 120° C. for 72 h. After cooling to room temperature the reaction mixture was partitioned between ethyl acetate (50 ml) and water (30 ml). The organic layer was separated. The aqueous layer was extracted with two 50-ml portions of ethyl acetate. The combined organic layers were washed with brine (30 ml), dried over anhydrous sodium sulfate and concentrated in vacuo. The crude cis/trans-hydrazide was triturated in ethyl acetate (5 ml). The precipitate was collected by filtration and dried in vacuo to give the crude title compound (0.236 g, 23%) as white solid, which was used in the next step without further purification. MS m/e: 237 ([M+H]$^+$).

Thiolactam Intermediate of Formula (III)

7-Chloro-3,5-dihydrobenzo[e][1,4]oxazepine-2(1H)-thione a) 2-Bromo-N-(4-chloro-2-(hydroxymethyl)phenyl)acetamide

To a solution of (2-amino-5-chlorophenyl)methanol (4.30 g, 27.3 mmol) in dichloromethane (220 ml) was added 2-bromoacetyl bromide (6.06 g, 2.61 ml, 30.0 mmol) at 0-5° C. Stirring for 5 minutes was followed by dropwise addition of aqueous 2 M sodium carbonate solution (130 ml) during approximately 10 minutes. The cooling bath was removed, and stirring was continued for 2 h. The solvent was removed in vacuo. The aqueous residue was extracted with three 100-ml portions of ethyl acetate. The combined organic layers were washed with one 50-ml portion of brine, dried over anhydrous sodium sulfate and concentrated in vacuo to give the title compound (7.30 g, 96%) as light grey solid, which was used in the next step without purification. MS m/e: 276 ([M+H]$^+$).

b) 7-Chloro-3,5-dihydrobenzo[e][1,4]oxazepin-2(1H)-one

To a suspension of 2-bromo-N-(4-chloro-2-(hydroxymethyl)phenyl)acetamide (3.60 g, 12.9 mmol) in 2-propanol (129 ml) was added in small portions potassium tert-butoxide (3.77 g, 33.6 mmol) at 0-5° C. The reaction mixture was stirred for 90 minutes and subsequently poured on ice/water (500 ml). The precipitate was collected by filtration and washed with water. Residual water was removed by consecutive evaporation with two 50-ml portions of toluene to give the title compound (2.34 g, 92%) as light yellow solid. MS m/e: 196 ([M−H]$^-$).

c) 7-Chloro-3,5-dihydrobenzo[e][1,4]oxazepine-2(1H)-thione

To a suspension of 7-chloro-3,5-dihydrobenzo[e][1,4]oxazepin-2(1H)-one (3.01 g, 15.2 mmol) in tetrahydrofurane (102 ml) was added 2,4-bis-(4-methoxyphenyl)-1,3,2,4-dithiadiphosphetane-2,4-disulfide (3.45 g, 8.53 mmol) at room temperature. The reaction mixture was heated at reflux for 4 h. After cooling to room temperature the solvent was evaporated and the residue was crystallized from hot ethanol to give the title compound (1.96 g, 60%) as light yellow solid. MS m/e: 211.6 ([M−H]$^-$).

General Procedure V: Condensation of Hydrazide and Thiolactam to Triazole

A mixture of a hydrazide derivative of formula (II) (1-1.5 eq) and a thiolactam of formula (III) (1 eq) in n-butanol (0.1-0.2 M) is heated at reflux for 16-72 h. After cooling to room temperature the solvent is evaporated and the residue is purified by flash-chromatography to give a compound of formula (I).

Example 1 trans-8-Chloro-1-(4-isopropoxy-cyclohexyl)-4H,6H-5-oxa-2,3,10b-triaza-benzo[e]azulene The title compound was obtained as white solid in 57% yield using general procedure V.
Hydrazide: trans-4-Isopropoxy-cyclohexanecarboxylic acid hydrazide
Thiolactam: 7-Chloro-3,5-dihydrobenzo[e][1,4]oxazepine-2(1H)-thione
MS m/e: 362 ([M+H]$^+$)

Example 2 trans-1-(4-sec-Butoxy-cyclohexyl)-8-chloro-4H,6H-5-oxa-2,3,10b-triaza-benzo[e]azulene The title compound was obtained as off-white solid in 63% yield using general procedure V.
Hydrazide: (RS)-trans-4-sec-Butoxy-cyclohexanecarboxylic acid hydrazide
Thiolactam: 7-Chloro-3,5-dihydrobenzo[e][1,4]oxazepine-2(1H)-thione
MS m/e: 376 ([M+H]$^+$)

Example 3 trans-8-Chloro-1-(4-cyclopentyloxy-cyclohexyl)-4H,6H-5-oxa-2,3,10b-triaza-benzo[e]azulene The title compound was obtained as off-white solid in 72% yield using general procedure V.
Hydrazide: trans-4-Cyclopentyloxy-cyclohexanecarboxylic acid hydrazide
Thiolactam: 7-Chloro-3,5-dihydrobenzo[e][1,4]oxazepine-2(1H)-thione
MS m/e: 388 ([M+H]$^+$)

Example 4 trans-8-Chloro-1-(4-phenoxy-cyclohexyl)-4H,6H-5-oxa-2,3,10b-triaza-benzo[e]azulene The title compound was obtained as white solid in 75% yield using general procedure V.
Hydrazide: trans-4-Phenoxy-cyclohexanecarboxylic acid hydrazide
Thiolactam: 7-Chloro-3,5-dihydrobenzo[e][1,4]oxazepine-2(1H)-thione
MS m/e: 396 ([M+H]$^+$)

Example 5 trans-8-Chloro-1-[4-(pyridin-2-yloxy)-cyclohexyl]-4H,6H-5-oxa-2,3,10b-triaza-benzo[e]azulene The title compound was obtained as off-white solid in 71% yield using general procedure V.
Hydrazide: trans-4-(Pyridin-2-yloxy)-cyclohexanecarboxylic acid hydrazide
Thiolactam: 7-Chloro-3,5-dihydrobenzo[e][1,4]oxazepine-2(1H)-thione
MS m/e: 397 ([M+H]$^+$)

Example 6 trans-8-Chloro-1-[4-(pyrazin-2-yloxy)-cyclohexyl]-4H,6H-5-oxa-2,3,10b-triaza-benzo[e]azulene The title compound was obtained as off-white solid in 37% yield using general procedure V.
Hydrazide: trans-4-(Pyrazin-2-yloxy)-cyclohexanecarboxylic acid hydrazide
Thiolactam: 7-Chloro-3,5-dihydrobenzo[e][1,4]oxazepine-2(1H)-thione
MS m/e: 398 ([M+H]$^+$).

What is claimed:
1. A compound of formula I

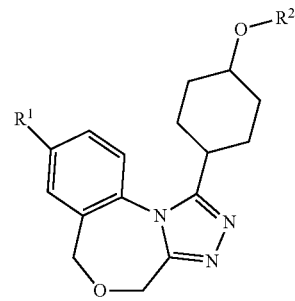

wherein
$R^1$ is halogen, and
$R^2$ is selected from the group consisting of
 i) heteroaryl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl;
 ii) aryl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl;
 iii) $C_{3-7}$-cycloalkyl, unsubstituted or substituted by 1 to 3 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy, $C_{1-6}$-alkoxy-$C_{1-6}$-alkyl and hydroxy-$C_{1-6}$-alkyl; and
 iv) $C_{1-6}$-alkyl, unsubstituted or substituted by 1 to 3 substituents individually selected from the group consisting of OH, halogen, cyano, $C_{1-6}$-alkoxy and halogen-$C_{1-6}$-alkoxy;
or a pharmaceutically acceptable salt thereof.

2. The compound of claim 1, wherein $R^1$ is chloro.

3. The compound of claim 2, wherein $R^2$ is selected from the group consisting of unsubstituted heteroaryl, unsubstituted aryl, unsubstituted $C_{3-7}$-cycloalkyl and unsubstituted $C_{1-6}$-alkyl.

4. The compound of claim 3, wherein $R^2$ is selected from pyridinyl, pyrazinyl, phenyl, cyclopentyl, isopropyl or sec-butyl.

5. A compound of claim 1, selected from the group consisting of
 8-Chloro-1-(4-isopropoxy-cyclohexyl)-4H,6H-5-oxa-2,3,10b-triaza-benzo[e]azulene,
 1-(4-sec-Butoxy-cyclohexyl)-8-chloro-4H,6H-5-oxa-2,3,10b-triaza-benzo[e]azulene,
 8-Chloro-1-(4-cyclopentyloxy-cyclohexyl)-4H,6H-5-oxa-2,3,10b-triaza-benzo[e]azulene,
 8-Chloro-1-(4-phenoxy-cyclohexyl)-4H,6H-5-oxa-2,3,10b-triaza-benzo[e]azulene,
 8-Chloro-1-[4-(pyridin-2-yloxy)-cyclohexyl]-4H,6H-5-oxa-2,3,10b-triaza-benzo[e]azulene, and
 8-Chloro-1-[4-(pyrazin-2-yloxy)-cyclohexyl]-4H,6H-5-oxa-2,3,10b-triaza-benzo[e]azulene
or a pharmaceutically acceptable salt thereof.

6. A pharmaceutical composition comprising a compound of formula I according to claim 1 and a pharmaceutically acceptable carrier and/or a pharmaceutically acceptable auxiliary substance.

* * * * *